United States Patent [19]

Urbas

[11] Patent Number: 4,820,880

[45] Date of Patent: Apr. 11, 1989

[54] PROCESS FOR THE PRODUCTION OF 3,4-DIDEOXYHEXITOL

[75] Inventor: Branko Urbas, Darien, Ill.

[73] Assignee: Michigan Biotechnology Institute, Lansing, Mich.

[21] Appl. No.: 50,650

[22] Filed: May 18, 1987

[51] Int. Cl.$^4$ .............................................. C07C 27/00
[52] U.S. Cl. ...................................... 568/861; 568/863
[58] Field of Search ................................ 568/861, 863

[56] References Cited

U.S. PATENT DOCUMENTS 3,040,062 6/1962 Hales ..................................... 568/861
3,083,236 3/1983 Utne et al. ........................... 568/861

OTHER PUBLICATIONS

Zartman and Adkins, *J. Am. Chem. Soc.*, 55, 4559–4563 (1933).
Gorin and Perlin, *Can. J. Chem.*, 36, 661–666 (1958).
Kuszmann and Sohar, *Carbohydrate Research*, 83, 63–72 (1980).
Lenth and DuPuis, *Ind. Eng. Chem.*, 37, 152–157 (1945).

*Primary Examiner*—John M. Ford
*Assistant Examiner*—Robert C. Whittenbaugh
*Attorney, Agent, or Firm*—Quarles & Brady

[57] ABSTRACT

A process for the production of 3,4-dideoxyhexitol and for its cyclodehydration to 2,5-bis(hydroxymethyl)tetrahydrofuran. The 3,4-dideoxyhexitol is obtained by hydrogenolysis in the presence of a copper chromite catalyst, of hexitols, or of compound which undergo reaction with hydrogen to give hexitols.

2 Claims, No Drawings

PROCESS FOR THE PRODUCTION OF 3,4-DIDEOXYHEXITOL

FIELD OF THE INVENTION

This invention relates to a process for the preparation of 3,4-dideoxyhexitol by the hydrogenolysis of hexitols in the presence of a copper chromite catalyst. This product undergoes cyclodehydration to give 2,5-bis(hydroxymethyl)tetrahydrofuran.

BACKGROUND OF THE INVENTION

Compounds containing two or more hydroxyl groups find use in a broad range of industrial applications. They are key components in such materials as polyesters, urethane foams and resins, and as intermediates for the preparation of surfactants. Two compounds having potential for use in such applications are 3,4-dideoxyhexitol and 2,5-bis(hydroxymethyl)tetrahydrofuran. However, previous methods for the preparation of these compounds have been too costly to be of commercial interest.

In 1933, Zartman and Adkins, *J. Am. Chem. Soc.*, 55, 4559–4563 (1933), reported the hydrogenolysis of sugars using copper-chromium oxide in ethanol solution at about 300 atmospheres pressure. The main product of this reaction was propylene glycol. Smaller amounts of other alcohols were formed in this reaction. Certain of the sugars gave small amounts of a tetrahydroxy compound, tentatively identified as 3,4-dideoxyhexitol (hexanetetrol-1,2,5,6).

Later, Gorin and Perlin, *Can. J. Chem.*, 36, 661–666 (1958) obtained 3,4-dideoxyhexitol in 4.3% yield by hydrogenolysis of 1,2-0-isopropylidene-D-glucofuranose. Still later, Kuszmann and Sohar, *Carbohydrate Research*, 83, 63–72 (1980), disclosed a multistep process for the conversion of mannitol to 3,4-dideoxy-D-threo-hexitol and for the conversion of glucitol into 3,4-dideoxy-erythro-hexitol. None of these methods are practical as a commercial synthesis of 3,4-dideoxyhexitol.

U.S. Pat. Nos. 3,040,062 and 3,083,236 disclose the preparation of 2,5-bis(hydroxymethyl)tetrahydrofuran by the catalytic hydrogenation of 5-(hydroxymethyl)-furfural, an expensive starting material.

The present invention involves the discovery that certain sugars or hexitols can be converted directly to 3,4-dideoxyhexitol in greatly improved yields when the starting materials are subjected to hydrogenolysis in the presence of a suitable catalyst. The hexitol is readily dehydrated with ring closure to give 2,5-bis(hydroxymethyl)tetrahydrofuran.

SUMMARY OF THE INVENTION

In accordance with this invention, there is provided a process for the production of 3,4-dideoxyhexitol which comprises heating with agitation a solution of a hexitol, or a compound which yields a hexitol upon reaction with hydrogen, in an organic solvent with hydrogen at a pressure of at least about 50 atmospheres and at a temperature of from about 180° C. to about 230° C. in the presence of a copper chromite catalyst until hydrogen uptake is complete.

Further, in accordance with this invention, there is provided a process for the production of 2,5-bis(hydroxymethyl) tetrahydrofuran which comprises heating 3,4-dideoxyhexitol in the presence of copper chromite or an acid catalyst.

DETAILED DESCRIPTION OF THE INVENTION

The starting materials used in the practice of this invention are hexitols or compounds which yield a hexitol upon reaction with hydrogen. Exemplary hexitols include sorbitol, mannitol, and dulcitol. Compounds which yield hexitol upon reaction with hydrogen include the 6-carbon monosaccharides, such as glucose, galactose, and fructose, as well as 12-carbon disaccharides, such as sucrose, maltose, and lactose.

Copper chromite catalysts are used in the hydrogenolysis process of this invention. Preferred catalysts are those in which the percent by weight of CuO is greater than the percent by weight of $Cr_2O_3$. The most preferred catalysts are those in which the copper chromite consists of about 80–85% by weight of CuO. Sufficient catalyst is used to give complete hydrogenolysis in a reasonable time. From about 1 to about 20, preferably from about 5 to about 15, parts by weight of catalyst per 100 parts by weight of starting material are suitable for this purpose.

In the practice of this invention, the hexitol, or compound which yields a hexitol upon reaction with hydrogen, is dissolved in an organic solvent. Any organic solvent which dissolves starting material under the conditions used for the hydrogenolysis, and which does not react with the starting material or reaction products, may be used. Suitable solvents include monohydric alcohols containing up to about 6 carbon atoms, glycols, and monoalkyl ethers of glycols. It is preferable to use a solvent which does not generate excessive vapor pressure under the conditions for carrying out the hydrogenolysis. It is also preferred to use a solvent which has a boiling point that permits its separation from the desired products of the hydrogenolysis by fractional distillation. Monoalkyl ethers of ethylene glycol, such as ethylene glycol monomethyl ether and ethylene glycol monoethyl ether, are particularly useful solvents.

The amount of solvent used can vary as long as there is sufficient solvent present to dissolve the compound undergoing hydrogenolysis. Highly concentrated solutions tend to slow the rate of hydrogenolysis, while very dilute solutions require expensive concentration before the product can be isolated. For these reasons, it is preferred to carry out the hydrogenolysis reaction in mixtures containing from about 10 to about 20 parts by weight of solvent for each part by weight of starting material. It is also important to use solvents which are essentially free from water. Water decreases the rate of hydrogenolysis and reduces selectivity for 3,4-dideoxyhexitol.

In the practice of the hydrogenolysis process of the present invention, the hexitol, or compound which yields a hexitol upon reaction with hydrogen, plus a suitable solvent is stirred with the copper chromite catalyst under hydrogen at a pressure of at least about 50 atm. Higher pressures may also be employed, but there is little advantage to using hydrogen pressures above about 100 atm.

As noted above, suitable temperatures for carrying out the reaction are between about 180° C. and about 230° C. While the reaction can be carried out at lower temperatures, it proceeds very slowly under those conditions. At temperatures above 230° C., the 3,4-dideoxyhexitol undergoes other reactions, such as dehydration, thereby lowering the yield of the desired product.

The 3,4-dideoxyhexitol prepared by the process of this invention is conveniently cyclodehydrated to form 2,5-bis(hydroxymethyl)tetrahydrofuran. This gives a convenient and economical process for the preparation of this dihydroxy compound. The cyclodehydration reaction is catalyzed by either copper chromite or a Lewis acid, or mixtures of these catalysts. It is conveniently carried out by heating the 3,4-dideoxyhexitol in a solvent in the presence of the catalyst. The solvent may be one which forms an azeotrope with water, and the dehydration can be run under conditions in which the water is continuously removed and the solvent is returned to the reaction mixture.

The 3,4-dideoxyhexitol formed by the process of this invention is a mixture of the threo and erythro forms. When this mixture is dehydrated according to the process of this invention, it gives a mixture of cis- and trans-2,5-bis(hydroxymethyl)tetrahydrofuran. The presence of these two components in the mixture is shown by cyclodehydration reactions of the separated threo and erythro isomers. The threo isomer gives cis2,5-bis(hydroxymethyl)tetrahydrofuran, whereas, the erythro isomer yields the trans-2,5-bis(hydroxymethyl)tetrahydrofuran.

The invention is further illustrated by the following examples in which all parts and percentages are by weight unless otherwise indicated.

EXAMPLE 1

A suspension of 50 g of sorbitol in 480 g of ethylene glycol monomethyl ether was placed in a 1000-ml autoclave with magnetic drive (MAGNA DASH, Model MB-1005, available from Autoclave Engineers, Erie, Pennsylvania). To this suspension was added 5 g of copper chromite catalyst containing 85% CuO and 15% $Cr_2O_3$ by weight (Harshaw Cu-0211P, available from the Harshaw Chemical Co., Cleveland, Ohio). The autoclave was closed and flushed three times with nitrogen at 14 atm and then charged with hydrogen at 136 atm. The mixture was stirred at 1000 rpm and heated to 200° C. During the period of about 3 hours, the pressure rose to about 184 atm and then dropped to about 150 atm when hydrogen uptake ceased. After the material was removed from the reactor, it was filtered and analyzed by HPLC (high performance liquid chromatography) (Bio-Rad Aminex HPX-57H cation-resin column) and carbon-13 NMR spectroscopy. The yield of 3,4-dideoxyhexitol was 11.7 g (28.3%). By-products of the reaction included ethylene glycol, propylene glycol, 1,2-butanediol, 1,2-hexanediol, and 1,2,6-trihydroxyhexane.

EXAMPLE 2

A suspension of 10 g of copper chromite catalyst as in Example 1 in 483 g of ethylene glycol monomethyl ether was placed in the 1000-ml autoclave and the suspension was adjusted to a pH of 10 with 50 μl of 50% NaOH solution. The reactor was flushed three times with nitrogen and then charged with hydrogen at 68 atm. The mixture was stirred at 1000 rpm and heated at 260° C. for 2 hours. The mixture was cooled to room temperature, charged with 50 g of sorbitol and then subjected to hydrogenolysis as in Example 1. In this case, hydrogen of initial pressure of 68 atm was used. Hydrogenolysis was carried out with stirring at 200° C. until the hydrogen uptake stopped (about 4 hours). During this period, the pressure of the reactor rose to about 95 atm and then dropped to about 61 atm. HPLC and carbon-13 NMR spectroscopy indicated that the yield of 3,4-dideoxyhexitol was 16 g (38.2%). When the prereduced catalyst was examined by X-ray diffraction, it was found to contain cuprous oxide and metallic copper.

The 3,4-dideoxyhexitol can be separated from the reaction mixture by fractional distillation. The fraction boiling at 180°–190° C. (0.1 mm) is suitable for use as a polyol in many commercial applications. The carbon-13 NMR spectrum indicates that the 3,4-dideoxyhexitol is a mixture of the two isomeric forms, 3,4-dideoxy-threo-hexitol and 3,4-dideoxy-erythro-hexitol. The erythro isomer can be crystallized from the reaction mixture by cooling and diluting with ethanol. This isomer melted at 98°–99° C. after two crystallizations. The mother liquor from which the erythro isomer crystallized contained a mixture of erythro and threo isomers which was hard to separate by fractional crystallization.

EXAMPLE 3

The general procedure of Example 1 was repeated except the reaction was allowed to run for 23 hours at 200° C. and then the temperature of the reaction mixture was raised to 260° C. and reaction was continued for an additional 5 hours. Samples were removed periodically from the reaction mixture and analyzed by HPLC and carbon-13 spectroscopy. the results given in Table I show that the principal product formed at 200° C. is 3,4-dideoxyhexitol. when the reaction is prolonged and the temperature is raised, this material is largely converted to 2,5-bis(hydroxymethyl)tetrahydrofuran

TABLE I

| | HYDROGENOLYSIS OF SORBITOL[a] | | | | |
|---|---|---|---|---|---|
| Products (% of | 200° C. | | 260° C. | | |
| Reaction Mixture) | 5 hrs | 23 hrs | 24 hrs | 26 hrs | 28 hrs |
| 3,4-Dideoxyhexitol | 26.7 | 30.7 | 24.5 | 6.4 | 0.3 |
| 2,5-Bis(hydroxymethyl)-tetrahydrofuran[b] | 5.3 | 16.5 | 17.2 | 26.7 | 31.4 |

[a]Sorbitol (50 g) in 480 g ethylene glycol monomethyl ether, 5 g of copper chromite containing 80% CuO and 20% $Cr_2O_3$ by weight (CALSICAT E-113TU, Calsicat Division of Mallinckrodt Co., Erie, PA), hydrogen at 68 atm initial pressure.
[b]Contaminated with a small amount of 1,2,6-trihydroxyhexane.

EXAMPLE 4

The general procedure of Example 1 was followed using a copper chromite catalyst containing 45% CuO, 45% $Cr_2O_3$ and 4 to 6% BaO by weight (CALSICAT E-102P, Calsicat Division of Mallinckrodt Co., Erie, PA). The initial pressure of hydrogen was 136 atm and the hydrogenolysis was carried out at 228° C. for 2.5 hrs. The yield of 3,4-dideoxyhexitol was 10.8%.

EXAMPLE 5

Crude 3,4-dideoxyhexitol prepared as in Example 1 was dissolved in 10 parts of ethylene glycol monomethyl ether and heated with stirring in an autoclave in the presence of 0.1 part of copper chromite catalyst under hydrogen pressure at 260° C. for 21 hours. Analysis of the product by HPLC indicated that essentially all of the 3,4-dideoxyhexitol present in the crude starting material had been converted to 2,5-bis(hydroxymethyl)-tetrahydrofuran. This shows that the copper chromite catalyst is capable of catalyzing the cyclodehydration of 3,4-dideoxyhexitol.

EXAMPLE 6

A solution of 4 g of 3,4-dideoxy-erythro-hexitol and 5 μml of concentrated sulfuric acid and 40 ml of ethylene glycol monomethyl ether was stirred under reflux for 16 hours. The mixture was cooled to room temperature, neutralized with calcium carbonate, filtered and concentrated to a heavy liquid weighing 4 g. Distillation under reduced pressure gave a product boiling at 95° C. (0.1 mm). The product was trans-2,5-bis(hydroxymethyl)tetrahydrofuran; di-p-toluenesulfonate, m.p. 97°–98° C. reported m.p. 96°–99° C. (Wiggins and Wood, *J. Chem. Soc.*, 1566–1575 (1950)).

In a similar fashion, 3,4-dideoxy-threo-hexitol was dehydrated in the presence of sulfuric acid catalyst to give cis-2,5-bis(hydroxymethyl)tetrahydrofuran; di-p-toluenesulfonate, m.p. 128°–129° C., reported m.p. 128°–130° C. (Cope and Baxter, *J. Am. Chem. Soc.*, 77, 393–396 (1955)).

Thus, it is apparent that there has been provided, in accordance with the invention, an improved process for the production of 3,4-dideoxyhexitol and for its conversion to 2,5-bis(hydroxymethyl)tetrahydrofuran. While the invention has been described in conjunction with specific embodiments thereof, it is evident that many alternatives, modifications, and variations will be apparent to those skilled in the art in light of the foregoing description. Accordingly, it is intended to include all such alternatives, modifications, and variations as set forth within the spirit and scope of the appended claims.

What is claimed is:

1. In the process of producing 3,4-dideoxyhexitol from a member selected from a hexitol and a compound which yields hexitol upon reaction with hydrogen, which method comprises heating said member in an organic solvent with hydrogen, under a pressure of at least about 50 atmospheres, in the presence of a copper chromite catalyst until hydrogen uptake is complete; the improvement which comprises employing a copper chromite catalyst which contains 80–85% by weight of CuO and which produces superior yields of 3,4-dideoxyhexitol.

2. In the process of claim 1, the improvement which comprises employing a copper chromite catalyst contaning 80–85% by weight of CuO which has been heated with hydrogen under pressure so that it contains metallic copper.

* * * * *